United States Patent [19]

Lacefield

[11] 4,048,312
[45] Sept. 13, 1977

[54] 2,4-DIAMINOQUINAZOLINES AS ANTITHROMBOTIC AGENTS

[75] Inventor: William B. Lacefield, Indianapolis, Ind.

[73] Assignee: Eli Lilly and Company, Indianapolis, Ind.

[21] Appl. No.: 637,781

[22] Filed: Dec. 4, 1975

Related U.S. Application Data

[62] Division of Ser. No. 411,115, Oct. 30, 1973, Pat. No. 3,956,495.

[51] Int. Cl.² .................. A61K 31/535; A61K 31/505
[52] U.S. Cl. .............................. 424/248.56; 424/251; 260/256.4 Q; 544/119; 544/80
[58] Field of Search .............................. 424/248, 251

[56] References Cited

U.S. PATENT DOCUMENTS

| 2,794,018 | 5/1957 | Spinks et al. | 260/256.4 |
| 2,945,859 | 7/1960 | Hitchings et al. | 260/256.4 |
| 3,511,836 | 5/1970 | Hess | 424/251 |
| 3,772,295 | 11/1973 | Robba et al. | 424/251 |

FOREIGN PATENT DOCUMENTS 2,121,031   11/1972   Germany

OTHER PUBLICATIONS

Roch et al., Chemical Abstracts 78:29808r, (1973).

Primary Examiner—Norman A. Drezin
Attorney, Agent, or Firm—William E. Maycock; Everet F. Smith

[57] ABSTRACT

2,4-Diaminoquinazolines are employed as antithrombotic agents and have the following general formula:

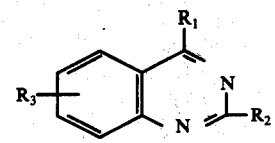

wherein $R_1$ and $R_2$ are monovalent groups independently selected from the group consisting of a.

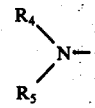

wherein $R_4$ and $R_5$ independently are selected from the group consisting of hydrogen, alkyl, and cycloalkyl, with the proviso that both $R_4$ and $R_5$ cannot be cycloalkyl, b.

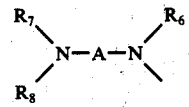

wherein $R_6$, $R_7$, and $R_8$ independently are selected from the group consisting of hydrogen and alkyl, and A is a divalent organic group having from two to about six carbon atoms such that the two nitrogen atoms are separated by at least two carbon atoms, and c. heterocyclic-amino, and $R_3$ is a monovalent group selected from the group consisting of hydrogen, halogen, and alkyl.

23 Claims, No Drawings

2,4-DIAMINOQUINAZOLINES AS ANTITHROMBOTIC AGENTS

This is a division of application Ser. No. 411,115, filed Oct. 30, 1973, now U.S. Pat. No. 3,956,495.

BACKGROUND OF THE INVENTION

This invention is related to 2,4-diaminoquinazolines. More particularly, this invention is related to the use of 2,4-diaminoquinazolines as antithrombotic agents.

A thrombus generally is defined as a plug or clot in a blood vessel or in one of the cavities of the heart, with said plug or clot remaining at the point of formation. When a thrombus is either free-floating in the blood stream or has been removed by the blood stream to a new location, it is referred to as an embolus. These two entities are responsible for a variety of disorders which are generally termed thromboembolic diseases. Such diseases include phlebothrombosis, thrombophlebitis, pulmonary embolism, retinal thrombosis, myocardial infarction, and cerebral infarction, among others.

The chemoprophylactic or chemotherapeutic management of thromboembolic diseases generally involves compounds which fall into one of three categories: (1) platelet aggregation inhibitors, (2) anticoagulants, and (3) fibrinolytic agents. The chemotherapeutic use of fibrinolytic agents is based upon the fact that fibrin frequently forms the primary structural support of a clot. Dissolution of the fibrin should result in lysis of the clot with restoration of blood flow. Anti-coagulants and platelet aggregation inhibitors, on the other hand, generally are employed prophylactically. Anticoagulants are more effective in the treatment of venous thrombosis than arterial thrombosis because of slower blood flow on the venous side which permits coagulation factors, not platelets, to play an important role. While anticoagulants might not prevent the formation of a platelet-dominated thrombosis in the arterial circulation, they certainly can inhibit the stabilization and extension of that thrombosis. However, the successful prophylaxis of arterial thrombosis must deal with the etiologic role of the platelet. The value of platelet function inhibitors in venous thrombosis will be reflected by the extent to which platelets are involved in the formation of those thrombi. Certainly, within the circulatory system, there are regions of stasis in which fibrin formation would be virtually the sole participant in thrombosis, and other regions of high hemodynamic activity where the platelet nidus alone could block the vessel. Consequently, the search for new platelet aggregation inhibitors continues.

SUMMARY OF THE INVENTION

In accordance with the present invention, a method for inhibiting platelet aggregation is provided which comprises administering to a warm-blooded animal an effective and nontoxic amount of a 2,4-diaminoquinazoline having the following general formula:

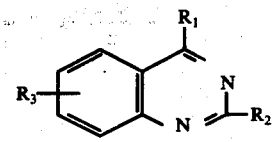

wherein $R_1$ and $R_2$ are monovalent groups independently selected from the group consisting of

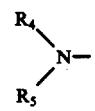

wherein $R_4$ and $R_5$ independently are selected from the group consisting of hydrogen, $C_1$–$C_6$ alkyl, and cycloalkyl having fewer than about 12 carbon atoms, with the proviso that both $R_4$ and $R_5$ cannot be cycloalkyl,

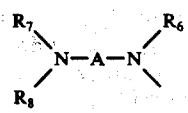

wherein $R_6$, $R_7$, and $R_8$ independently are selected from the group consisting of hydrogen and $C_1$–$C_6$ alkyl, and A is a divalent organic group having from two to about six carbon atoms such that the two nitrogen atoms are separated by at least two carbon atoms, and (c) heterocyclic-amino, and $R_3$ is a monovalent group selected from the group consisting of hydrogen, halogen, and $C_1$–$C_3$ alkyl. As used herein, the term "heterocyclic-amino" is intended to mean a saturated nitrogen heterocyclic group which is attached to the quinazoline moiety by means of a hetero nitrogen atom, wherein said nitrogen heterocyclic group contains fewer than about three rings and up to about three hetero atoms, of which one must be nitrogen and any others present independently are selected from the group consisting of nitrogen and oxygen, and the total number of atoms present is no more than about 12.

DETAILED DESCRIPTION OF THE INVENTION

In general, the 2,4-diaminoquinazolines are prepared by known methods, usually from 2,4-dichloroquinazoline; see, for example, Postovskii and Goncharova, *Zh. Obshch. Khim.*, 32, 3323 (1962). 2,4-Dichloroquinazoline in turn is readily prepared from 2,4(1H,3H)-quinazolinedione, by the method of Curd, et al., *J. Chem. Soc.*, 1947, 775. The following reaction scheme illustrates preferred procedures employed in the preparation of the 2,4-diaminoquinazolines:

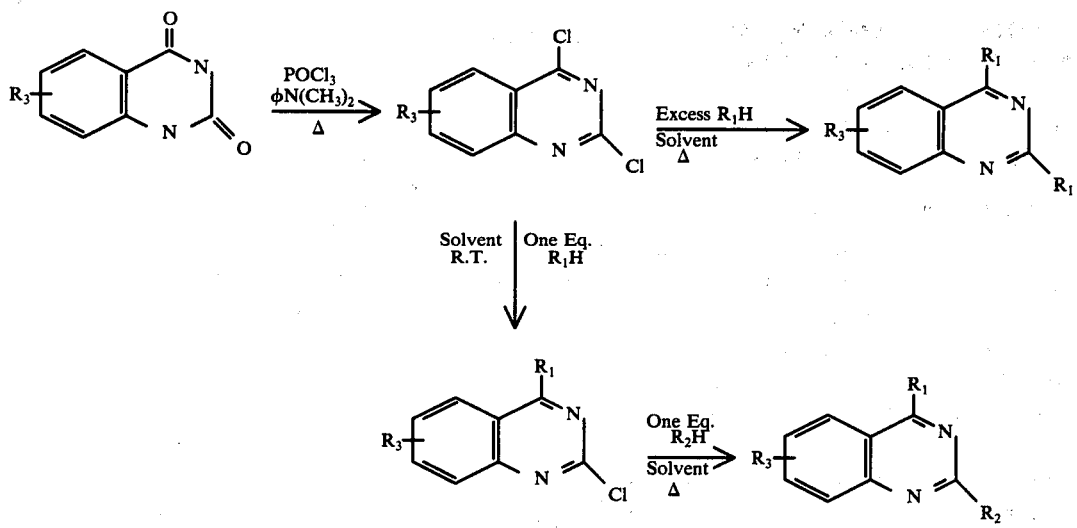

Briefly, a 2,4(1H,3H)-quinazolinedione is refluxed with excess phosphorus oxychloride in the presence of N,N-dimethylaniline (or other suitable tertiary amine) to give the corresponding 2,4-dichloroquinazoline. If $R_1$ and $R_2$ are to be the same, the 2,4-dichloroquinazoline is treated with excess amine, preferably in a suitable solvent, such as tetrahydrofuran, and usually at an elevated temperature which normally is the reflux temperature of the solvent, to give the 2,4-diaminoquinazoline. If $R_1$ and $R_2$ are to be different, the 2,4-dichloroquinazoline is treated with one equivalent of amine, usually in a solvent and at room temperature, to give the corresponding 2-chloro-4-aminoquinazoline. The 2-chloro-4-aminoquinazoline then is treated with at least one equivalent of a second amine, again in a solvent and usually under elevated temperature, such as the reflux temperature of the solvent, to give the desired 2,4-diaminoquinazoline.

From the description of amines which follows, it should be obvious to one skilled in the art that the use in the above reaction scheme of amines having more than one nitrogen atom, each of which has at least one hydrogen atom, normally will result in a mixture of two or more isomers. Clearly, such a mixture must be purified in order to isolate the desired compound. Alternatively, appropriate blocking groups can be employed to eliminate or minimize unwanted isomers.

Examples of amines, i.e., compounds other than ammonia, which will give rise to $R_1$ and $R_2$ include, among others, methylamine, sec-butylamine, n-hexylamine, 2,3-dimethylbutylamine, diethylamine, ethyl-3,3-dimethylbutylamine, n-propylisopropylamine, 1,2-diaminoethane, 1,3-diaminopropane, 1,5-diaminopentane, 1,2-diaminopropane, 1-methylamino-2-amino ethane, 1-isohexylamino-3-amino-2,3-dimethylbutane, 1-ethylamino-4-aminobutane, 1-amino-2-methylaminoethane, 1-amino-2-di-n-propylaminoethane, 1-amino-5-diisopropylaminopentane, 1-ethylamino-3-isopropylaminopropane, 2-(2,3-dimethylbutylamino)-4-isopropylmethylamino-3-methylpentane cyclopropylamine, cyclohexylamine, cyclooctylamine, cyclobutylethylamine, cyclopentyl-3-methyl-2-pentylamine, 1-decalylamine, 2-decalylisobutylamine, 7-norbornyl-n-hexylamine, 1-adamantylamine, azetidine, pyrrolidine, oxazolidine, isoxazolidine, pyrazolidine, imidazolidine, morpholine, hexahydropyrimidine, piperazine, 4-methylpiperazine, piperidine, hexahydro-1,3,6-oxadiazepine, octahydro-1,5-diazocine, 3,4-dimethylenepiperidine, 2-azabicyclo[2.2.0]octane, 1-oxa-7-azaspiro[4.4]-nonane, octahydroskatole, decahydroisoquinoline, decahydroquinoxaline, and the like.

It should be understood that the foregoing list is illustrative only and is not intended to be limiting in any manner.

As indicated hereinbefore, $r_3$ is selected from the group consisting of hydrogen, halogen, and $C_1$–$C_3$ alkyl. Preferably, $R_3$ will be hydrogen, chlorine, or methyl, and most preferably will be in the 6-position.

From the foregoing, the 2,4-diaminoquinazolines useful in the method of the present invention clearly can have either identical or dissimilar substituents in the 2- and 4-positions. For example, the use of an excess of ammonia or one amine gives compounds having identical substituents in the 2- and 4-positions, such as 2,4-diaminoquinazoline, 2,4-diamino-6-methylquinazoline, 2,4-diamino-7-isopropylquinazoline, 2,4-bis-n-butylaminoquinazoline, 2,4-bis(dimethylamino)quinazoline, 2,4-bis(diethylamino)-5-fluoroquinazoline, 2,4-bis(3-amino-2-methylpropylamino)quinazoline, 2,4-bis(2-aminoethylmethylamino)-quinazoline, 2,4-bis(2-methylaminoethylamino)-6-ethylquinazoline, 2,4-bis(2-diethylaminoethylamino)-6-methylquinazoline, 2,4-bis[3-(3-ethylbutylamino)butylethylamino]quinazoline, 2,4-bis-(3-di-n-hexylaminopropyl-sec-butylamino)-quinazoline, 2,4bis-(cyclopropylamino)-8-iodoquinazoline, 2,4-bis(3-methylcyclohexylisopropylamino)-quinazoline, 2,4-bis(1-norbornylmethylamino)-7-bromoquinazoline, 2,4-bis(1-adamantylamino)quinazoline, 2,4-bis(1-decalylmethylamino)quinazoline, 2,4-bispyrrolidinylquinazoline, 2,4-bispyrrolidinyl-4-propylquinazoline, 2,4-bispiperidinoquinazoline, 2,4-bispiperidino-6-chloroquinazoline, 2,4-bispiperidino-5-isopropylquinazoline, 2,4-bismorpholinoquinazoline, 2,4-bismorpholino-8-ethylquinazoline, 2,4-bis-(7-azabicyclo[4.2.0]-7-octyl)-6-chloroquinazoline 2,4-bis-(1-oxa-7-azaspiro[4.4]-7-nonyl)-6-methylquinazoline, 2,4-bishexahydroindolinylquinazoline, 2,4-bisdecahydroisoquinolyl-7-iodoquinazoline, 2,4-bishexahydrobenzoxazolylquinoline, 2,4-bisdecahydropyrido[4,3-d]-pyrimidin-3-yl-6-chloroquinazoline, and the like, to name just a few.

On the other hand, the use of two different amines in a stepwise sequence gives 2,4-diaminoquinazolines having dissimilar substituents in the 2- and 4-positions. Examples of such compounds include, among others, 2-amino-4-cyclohexylaminoquinazoline, 2-cyclohexylamino-4-aminoquinazoline, 2-aminoethylamino-6-methylquinazoline, 2-neohexylamino-4-amino-5-chloroquinazoline, 2-morpholino-4-(2-diethylaminoethylamino)-quinazoline, 2-(1-decalylmethylamino)-4-methylneohexylamino-8-ethylquinazoline, 2-(2-diethylaminoethylamino)-4-morpholino-7-isopropyl-quinazoline, 2-amino-4-(diisopropylamino)-6-chloroquinazoline, 2-(cyclopentyl-3-methyl-2-pentylamino-4-(1-oxa-7-azaspiro[4.4]non-7-yl)quinazoline, 2-(2-azabicyclo-[2.2.0]oct-2-yl)-4-amino-7-iodoquinazoline, 2-n-butylamino-4-( 3-decahydroquinazolinyl)-quinazoline, 2-morpholino-4-aminoquinazoline, 2-amino-4-morpholinoquinazoline, 2-(4-methylpiperazinyl)-4-aminoquinazoline, 2-(2-aminoethylamino)-4-morpholine-6-propylquinazoline, 2-morpholino-4-(2-aminoethylamino) -7-fluoro quinazoline, 2-pyrrolidinyl-4-(2-diethylaminoethylamino)quinazoline, 2-morpholino-4-(2-diethylaminoethylamino)-quinazoline, 2-diethylamino-4-morpholino-6-bromoquinazoline, 2-methylisobutylamino-4-cyclohexylmethylaminoquinazoline, 2-(1-adamantylamino)-4-azetidinylquinazoline, and the like.

Referring to the general formula for the 2,4-diaminoquinazolines as defined hereinbefore, the preferred 2,4-diaminoquinazolines are those wherein $R_4$ and $R_5$ independently are selected from the group consisting of hydrogen, $C_1$–$C_3$ alkyl, and cycloalkyl, with the proviso that when either $R_4$ or $R_5$ is hydrogen, the other remaining group cannot be $C_1$–$C_3$ alkyl; $R_6$, $R_7$, and $R_8$ independently are selected from the group consisting of hydrogen and $C_1$–$C_3$ alkyl; A is a polymethylene group; heterocyclic-amino is a monocyclic group; and $R_3$ is selected from the group consisting of hydrogen, chlorine, and methyl. Examples of such preferred compounds include, among others, 2,4-diaminoquinazoline, 2,4-diamino-6-methylquinazoline, 2,4-bis(dimethylamino)-7-chloroquinazoline, 2,4-diisopropylquinazoline, 2,4-bis(2-bis(2-diethylaminoethylmethyamino)quinazoline, 2,4-bis(cyclopropylamino)-8-methylquinazoline, 2,4-bis(3-methylcyclohexyl-n-propylamino)quinazoline, 2,4-bis(3-aminopropylamino)quinazoline, 2,4-bis(1-adamantylamino)quinazoline, 2,4-bismorpholinoquinazoline, 2,4-bispyrrolidinyl-6-methylquinazoline, 2-amino-4-cyclohexylaminoquinazoline, 2-cyclohexylamino-4-amino quinazoline, 2-aminoethylamino-4-morpholino-5-chloroquinazoline, 2-morpholino-4-(methyl-2-diethylaminoethylamino quinazoline, 2-(2-diethylaminoethylamino)-4-piperazinyl-7-methylquinazoline, and the like.

In a similar manner, the most preferred 2,4-diaminoquinazolines are those wherein $R_4$ and $R_5$ both are either hydrogen or identical $C_1$–$C_3$ alkyl groups or one of $R_4$ and $R_5$ is hydrogen and the remaining group is cycloalkyl; $R_6$ is hydrogen; $R_7$ and $R_8$ both are identical $C_1$–$C_3$ alkyl groups; A is a polymethylene group; heterocyclic-amino is a group which comprises either five-or six-membered heterocyclic rings containing one nitrogen atom, two nitrogen atoms, or one nitrogen atom and one oxygen atom; and $R_3$ is located in the 6-position and is selected from the group consisting of hydrogen, chloro, and methyl. Examples of most preferred 2,4-diaminoquinazolines include, among others, 2,4-diamino-6-methylquinazoline, 2,4-bis(dimethylamino)quinazoline, 2-amino-4-(diisopropylamino)-6-chloroquinazoline, 2-morpholino-4-amino-quinazoline, 2-(4-methylpiperazinyl)-4-aminoquinazoline, 2,4-bis(2-diethylaminoethylamino)-6-methylquinazoline, 2-(2-aminoethylamino)-4-morpholinoquinazoline, 2-pyrrolidinyl-4-(2-diethylaminoethylamino)quinazoline, 2-morpholino-4-(2-diethylaminoethylamino)-quinazoline, 2-morpholino-4-diethylaminoquinazoline, 2,4-bispyrrolidinylquinazoline, 2,4-bispiperidinoquinazoline, 2,4-bispiperidino-6-chloroquinazoline, 2,4-bispiperidino-6-methylquinazoline, 2-morpholino-4-cyclohexylaminoquinazoline, 2-morpholino-4-(1-adamantylamino)quinazoline, 2,4-bismorpholinoquinazoline, 2,4-bismorpholino-6-chloroquinazoline, 2,4-bismorpholino-6-methylquinazoline, 2-morpholino-4-(4-methylpiperazinyl)quinazoline, 2-(4-methylpiperazinyl)-4-morpholinoquinazoline, and the like.

It should be understood that all of the foregoing listings of 2,4-diaminoquinazolines are illustrative only and are not intended to be limiting in any manner.

It also should be understood that such terms as "2,4-diaminoquinazolines" are meant to include physiologically-acceptable salts thereof. Physiologically-acceptable salts are those salts of 2,4-diaminoquinazolines formed from anions which do not as a whole increase the toxicities of the compounds toward warm-blooded animals. Otherwise, the identity of the salt-forming anion is not critical, although in some instances an anion may be chosen which imparts special characteristics to the salt, such as improved solubility, ease of crystallization, and the like. Examples of suitable anions include, among others, fluoride, chloride, bromide, iodide, phosphate, sulfate, p-toluenesulfonate, acetate, and the like.

As stated hereinbefore, the 2,4-diaminoquinazolines possess antithrombotic activity and consequently find utility in the prophylaxis of thromboembolic disease. The 2,4-diaminoquinazolines also can be used as platelet aggregation inhibitors in stored blood. For this latter use, the compounds are employed at levels of from about 1 to about 250 $\mu$g/ml., and preferably at levels of from about 10 to about 100 $\mu$g/ml.

In the prophylaxis of thromboembolic diseases, the 2,4-diaminoquinazolines can be administered to warm-blooded animals parenterally, preferably intravenously. The compounds normally will be administered at levels of from about 1 to about 250 $\mu$g/ml., and preferably from about 1 to about 100 $\mu$g/ml. However, the compounds can be administered at levels up to the toxic dose. On the average, these levels of administration are approximately equivalent to a general range from about 0.05 to about 20 mg/kg., with the preferred range being approximately equivalent to from about 0.05 to about 10 mg/kg. Following procedures well known to those skilled in the art, the 2,4-diaminoquinazolines normally will be formulated into pharmaceutical compositions comprising the active ingredient in association with at least one pharmaceutically-acceptable carrier therefor. Such compositions generally are prepared by incorporating a 2,4-diaminoquinazoline in a liquid solution or suspension, except that suspensions are not employed for intravenous administrations. In such compositions, a 2,4-diaminoquinazoline ordinarily will present in an amount of at least 0.0001 and not more than about 50 percent by weight, based on the total weight of the composition.

In addition to a 2,4-diaminoquinazoline, the composition will contain a liquid, non-toxic pharmaceutical carrier for said compound. The pharmaceutical carrier can be a sterile liquid, such as water and oils, including petroleum, animal, vegetable, and synthetic oils, examples of such oils being peanut oil, soy bean oil, mineral oil, cod liver oil, and the like. In general, water, saline, and aqueous dextrose (glucose) and related sugar solutions are the preferred liquid carriers. Such sterile injectionable solutions ordinarily contain from about 0.5 to about 25, and preferably from about 5 to about 25 percent by weight of a 2,4-diaminoquinazoline.

Suitable pharmaceutical carriers are described in E. W. Martin, et al., "Remington's Pharmaceutical Sciences," 14th. Ed., Mack Publishing Company, Easton, Pa., 1965.

The activities of the 2,4-diaminoquinazolines relative to parenteral administration were demonstrated by the procedure of Herrmann, et al., *Proc. Soc. Exp. Biol. Med.*, 135, 100 (1970), and references cited therein. Said activities were demonstrated against both collagen-induced aggregation and ADP-induced aggregation and are summarized in Table 1.

TABLE I

Platelet Aggregation Inhibition In Vitro Test

Quinazoline

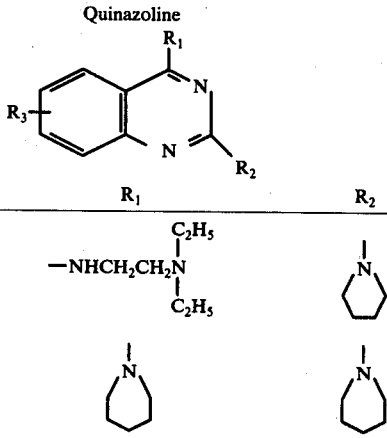

| $R_1$ | $R_2$ | $R_3$ | Conc.[a] | Dilution | % Inhibition (Collagen) | % Inhibition (ADP) |
|---|---|---|---|---|---|---|
| —NHCH$_2$CH$_2$N(C$_2$H$_5$)$_2$ |  (piperidine) | H | 10.4 | Undiluted[b] | $\geq 20$ | N.T.[c] |
|  (piperidine) |  (piperidine) | | 20.8 | 1:4[b] | $\geq 20$ | N.T. |
| | | H | 2.6 | Undiluted[b] | $\geq 20$ | N.T. |
| | | | 83.4 | 1:4[b] | $\geq 20$ | N.T. |
| —N(CH$_3$)$_2$ | —N(CH$_3$)$_2$ | H | 41.7 | 1:4[b] | $\geq 20$ | N.T. |
| —N(C$_2$H$_5$)$_2$ | 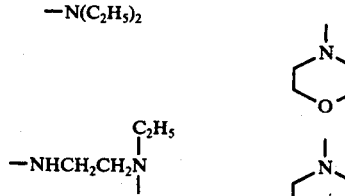 (morpholine) | H[e] | 10.4 | 1:4[b] | $\geq 20$ | N.T. |
| —NHCH$_2$CH$_2$N(C$_2$H$_5$)$_2$ | 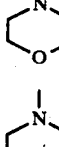 (morpholine) | H[e] | 41.7 | 1:4[b] | $\geq 20$ | N.T. |
|  (morpholine) | —NHCH$_2$CH$_2$NH$_2$ | H[e] | 83.4 | 1:4[b] | $\geq 20$ | N.T. |
|  (morpholine) |  (piperidine) | H | 41.7 | 1:4[b] | $\geq 20$ | N.T. |
| adamantyl-NH— |  (morpholine) | H[e] | 83.4 | 1:4[b] | $\geq 20$ | N.T. |
|  (morpholine) | (morpholine) | H | 10.4 | 1:4[b] | 35 | N.T. |
|  (piperazine) | (morpholine) | H | 5.2 | N.T. | N.T. | 51 |
| | | H | 41.7 | 1:4[b] | $\geq 20$ | N.T. |

TABLE I-continued
Platelet Aggregation Inhibition In Vitro Test

Quinazoline structure with substituents R1 (at 4-position), R2 (at 2-position), R3 (at benzene ring).

| R1 | R2 | R3 | Conc.[a] | Dilution | % Inhibition (Collagen) | % Inhibition (ADP) |
|---|---|---|---|---|---|---|
| 4-(N-CH3)morpholinyl (N-methyl) | 4-methylpiperazin-1-yl | H[e] | 2.6 | 1:32[d] | 30 | N.T. |
| —NH2 | piperazin-1-yl | H[e] | 83<br>83.4 | N.T.<br>1:4[b] | N.T.<br>≥20 | 44<br>N.T. |
| —NH2 | 4-methylpiperazin-1-yl (CH3) ... morpholino | H | 41.7 | 1:4[b] | ≥20 | N.T. |
| morpholino | morpholino | 6-CH3 | 167 | 1:32[d] | 62 | 29 |
| piperidino | piperidino | 6-CH3 | 167 | 1:32[d] | 21 | 5 |
| piperidino | piperidino | 6-Cl | 167 | 1:32[d] | 91 | 61 |
| morpholino | morpholino | 6-Cl | 167 | 1:32[d] | 25 | 3 |

[a] Concentration in μg/ml
[b] Dilution ratio of collagen stock suspension
[c] Not tested
[d] Dilution ratio of collagen stock solution
[e] As hydrochloride salt In addition to parenteral administration, it has been demonstrated that at least some of the 2,4-diaminoquinazolines can be administered enterally, preferably orally. For enteral administration, a 2,4-diaminoquinazoline normally will be formulated into a pharmaceutical composition comprising the active ingredient in association with at least one pharmaceutically-acceptable carrier therefor. Such compositions normally will consist of the active ingredient mixed with the carrier, or diluted by a carrier, or enclosed or encapsulated by a carrier in the form of a capsule, cachet, or other container. The carrier may be a solid, semi-solid, or liquid material which serves as a vehicle, excipient, coating agent, or medium for the active ingredient. Some examples of carriers which may be used are lactose, dextrose, sucrose, sorbitol, mannitol, starch, gum acacia, calcium phosphate, liquid paraffin, cocoa butter, oil of theobroma, alginates, tragacanth, gelatin, methyl cellulose, polyoxyethylene sorbitan monolaurate, methyl or propyl hydroxybenzoate, ethyl cellulose acetate phthalate, low viscosity acetyl cellulose acetate, paraffin wax, mineral wax, vegetable wax, vegetable gum, silicone rubber such as liquid polydimethylsiloxane rubber, plasticized polyvinyl chloride, plasticized polyethylene terephthalate, modified collagen, cross-linked hydrophilic polyether gel, cross-linked polyvinyl alcohol or cross-linked partially hydrolyzed polyvinyl acetate.

For enteral administration, the 2,4-diaminoquinazolines normally will be administered at levels in the range of from about 1 to about 150 mg/kg. Advantageously the 2,4-diaminoquinazolines are formulated in a dosage unit form containing from about 5 to about 500 mg., preferably from about 10 to about 150 mg., of the active ingredient. Examples of suitable dosage unit forms are tablets, hard or soft gelatin capsules, micro-capsules, and suppositories, as well as drug-dispensing systems comprising the active ingredient contained in a flexible, imperforate polymeric material through which the drug may be released slowly by diffusion. More generally, the term "dosage unit form" as used herein means a physically-discrete unit containing the active ingredient, generally in admixture with and/or enclosed by a pharmaceutical carrier, the quantity of active ingredient being such that one or more units normally are required for a single therapeutic administration.

That some of the 2,4-diaminoquinazolines can be administered orally has been demonstrated by an in vivo-invitro test procedure. Briefly, the test procedure is as follows: blood samples are obtained from a guinea pig prior to the oral administration of the test compound. The test compound then is administered orally and blood samples withdrawn one hour and three hours after dosing. Each blood sample is treated as described in the in vitro test. The test requires one control group of six animals and six animals per compound per dose. For a more detailed description, see Herrmann, et al., Proc. Soc. Exp. Biol. Med., 139, 548 (1972). The results of the in vivo-in vitro test are summarized in table II:

TABLE II

Platelet Aggregation Inhibition
In Vivo-In Vitro Test

| Quinazoline | | | | | % Inhibition of Aggregation to Collagen Challenge |
|---|---|---|---|---|---|
| $R_1$ | $R_2$ | $R_3$ | Dose[a] | Dilution[b] | % Inhibition |
| piperidino | piperidino | H | 12.5 | 1:4 | ≥ 20 |
| —NHCH$_2$CH$_2$N(C$_2$H$_5$)$_2$ | morpholino | H[c] | 100 | 1:4 | ≥ 20 |
| piperidino | piperidino | H | 50 | 1:4 | ≥ 20 |

[a]Dose in mg/kg
[b]Dilution ratio of stock suspension
[c]As dihydrochloride salt The toxicities of the 2,4-diaminoquinazolines vary over a wide range. For example, the highest dose which can be administered interperitoneally to mice without producing any deaths within a five-day period ranges from about 10 mg/kg. to about 1000 mg/kg. and perhaps higher. However, the 2,4-diaminoquinazolines are active in the in vitro test described hereinbefore at levels of from about 1/3 to about 1/150 of said highest dose. Consequently, the 2,4-diaminoquinazolines can be used parenterally at levels substantially below the toxic levels.

The present invention is further described, but not limited, by the following examples which illustrate preferred procedures for the preparation of the 2,4-diaminoquinazolines. Unless otherwise stated, all temperatures are in degrees centigrade.

EXAMPLE I

A mixture of 100 g of 2,4(1H,3H)-quinazolinedione, 300 ml of phosphorus oxychloride, and 45 ml of N,N-dimethylaniline was heated at reflux for 6 hours. The reaction mixture was cooled slightly and poured over ice. The resulting mixture, which consisted of about 6 liters, was divided between two four-liter separatory funnels and was extracted with a total of 6 liters of benzene. The benzene extracts were combined and washed successively with several volumes of water, 5 percent sodium bicarbonate solution, and then with water until the washes were neutral to litmus. The organic phases were combined, dried over anhydrous sodium sulfate, and filtered. The benzene was removed by distillation and the residue was crystallized from a solvent mixture consisting of 500 ml of benzene and 1,500 ml of hexane. Filtration afforded 72 g of a brown solid which was recrystallized from 2.5 liters of hexane to yield 43 g of pure 2,4-dichloroquinazoline; m.p. 116°-118°. The following analytical data were obtained:

Calculated for $C_8H_4Cl_2N_2$: C, 48.28; H, 2.03; Cl, 35.62; N, 14.07. Found: C, 47.99; H, 2.23; Cl, 35.39; N, 13.82.

The nuclear magnetic resonance spectrum supported the assigned structure. An additional 43 g of crude product was obtained by evaporation of the filtrates from the crystallization and recrystallization procedures.

EXAMPLE II

A mixture of 10 g of dimethylamine, 100 ml of ethanol, and 10 g of 2,4-dichloroquinazoline was heated at reflux for 0.5 hour. The solvent was removed by distillation. The oily residue which remained was dissolved in 100 ml of water. The aqueous solution was made alkaline with dilute sodium hydroxide solution. The resultant precipitate was collected by filtration, washed with water, and dried, giving 9 g of 2,4-bis(dimethylamino)quinazoline; mp 74°-76°. The following analytical data were obtained:

Calculated for $C_{12}H_{18}N_4$: C, 66.02; H, 8.31; N, 25.66. Found: C, 65.85; H, 8.43; N, 25.46.

The nuclear magnetic resonance spectrum was consistent with the assigned structure.

EXAMPLE III

Eight grams of 2,4-dichloroquinazoline was cautiously added to 25 ml of morpholine; a vigorous reaction ensued upon mixing. After the initial reaction subsided, the mixture was then heated to 110° overnight. The reaction mixture was poured into water, and the resulting aqueous solution was extracted with several portions of ether. The combined ether extracts were washed with water, dried over anhydrous sodium sulfate, and filtered. The filtrate was evaporated to dryness and the residue was recrystallized from aqueous ethanol, giving 8 g of 2,4-bismorpholinoquinazoline; m.p. 172°-174°. The following analytical data were obtained:

Calculated for $C_{18}H_{20}N_4O_2$: C, 63.98; H, 6.71; N, 18.65. Found: C, 64.21; H, 6.93; N, 18.59.

The nuclear magnetic resonance spectrum was consistent with the assigned structure.

EXAMPLE IV

Ten grams of 2,4-dichloroquinazoline was added carefully to a solution of 25 ml of pyrrolidine in 200 ml of tetrahydrofuran. The resulting mixture was heated at reflux overnight and then was poured into a mixture of ice and water. The resulting mixture was extracted several times with ether. The ether extracts were combined and washed with water. The ether phase then was dried over anhydrous sodium sulfate. The solvent was removed by distillation and the residue was recrystallized from a 1:1 benzene:hexane mixture to give 10.1 g of 2,4-bispyrrolidinylquinazoline; m.p. 127°-129°. The following analytical data were obtained:

Calculated for $C_{16}H_{20}N_4$: C, 71.61; H, 7.57; N, 20.88. Found C, 71.38; H, 4.82; N, 20.83.

The nuclear magnetic resonances spectrum was consistent with the assigned structure.

EXAMPLE V

The procedure of Example IV was repeated, except that the pyrrolidine was replaced with an equal volume of piperidine. The crude product was recrystallized from hexane to give 9.2 g of 2,4-bispiperidinoquinazoline; m.p. 128°-131°. The following analytical data were obtained:

Calculated for $C_{18}H_{24}N_4$: C, 72.94; H, 8.16; N, 18.90. Found: C, 72.90; H, 8.32; N, 18.69.

The nuclear magnetic resonance spectrum was consistent with the assigned structure.

EXAMPLE VI

A mixture of 4 g of 2,4-dichloro-6-methylquinazoline, 50 ml of tetrahydrofuran, and 20 ml of piperidine was heated at reflux for 6 hours. The reaction mixture was filtered to remove piperidine hydrochloride and the filtrate was diluted with a mixture of ice and water. The oil which separated crystallized when it was rubbed against the wall of the container. The solid was isolated by filtration, washed with water, dried, and recrystallized from ethanol. The yield of crude 2,4-bispiperidino-6-methylquinazoline was 5.7 g; m.p. 94°-98°. A second recrystallization from ethanol afforded 3.7 g of pure product; m.p. 95°-97°. The following analytical data were obtained;

Calculated for $C_{18}H_{26}N_4$: C, 73.51; H, 8.44; N, 18.05. From: C, 73.31: H, 8.53; N, 17.79.

EXAMPLE VII

Five grams of 2,4-dichloro-6-methylquinazoline and 25 ml of morpholine in 50 ml of tetrahydrofuran was heated at reflux overnight. The solid which had precipitated was removed by filtration and shown to be morpholine hydrochloride. The filtrate was evaporated to dryness and the residue triturated with water. The resulting solid was isolated by filtration and recrystallized from ethanol. The yield of 2,4-bismorpholino-6-methylquinazoline was 5.8 g; m.p. 147°-150°. The following analytical data were obtained:

Calculated for $C_{17}H_{23}N_4O_2$: C, 64.95; H, 7.05; N, 17.82. Found: C, 64.79; H, 6.93; N, 18.11.

The nuclear magnetic resonance spectrum substantiated the assigned structure.

EXAMPLE VIII

Four grams of 2,4,6-trichloroquinazoline was dissolved in 50 ml of tetrahydrofuran. The solution was cooled in an ice bath and 20 ml of piperidine was added with constant stirring. The reaction mixture was heated at reflux overnight and the solid which had precipitated was removed by filtration. The filtrate was evaporated to dryness and diluted with water. The oil which separated crystallized upon scratching. The solid was collected by filtration and recrystallized from ethanol to give 4.2 g of 2,4-bispiperidino-6-chloroquinazoline; m.p. 115°-118°. The following analytical data were obtained:

Calculated for $C_{18}H_{23}N_4Cl$: C, 65.34; H, 7.01; N, 16.93. Found: C, 65.41; H, 6.81; N, 16.69.

The nuclear magnetic resonance spectrum was consistent with the assigned structure.

EXAMPLE IX

The procedure of Example VIII was repeated, except that the piperidine was replaced with an equal volume of morpholine. Furthermore, the solid obtained upon evaporating the filtrate to dryness was recrystallized directly from ethanol. The yield of 2,4-bismorpholino-6-chloroquinazoline was 4.7 g; m.p. 138°-140°. The following analytical data were obtained:

Calculated for $C_{16}H_{19}N_4O_2Cl$: C, 57.40; H, 5.73; N, 16.73. Found: C, 57.63; H, 5.82; N, 16.59

The nuclear magnetic resonance spectrum was consistent with the assigned structure.

EXAMPLE X

A mixture of 16 g of 2,4-dichloroquinazoline and 300 ml of concentrated ammonium hydroxide was stirred at ambient temperature overnight. The solid which had precipitated was collected by filtration and was recrystallized from ethanol. The yield of 2-chloro-4-aminoquinazoline was 12 g; m.p. 227°-229°. The following analytical data were obtained:

Calculated for $C_8H_6ClN_3$: C, 53.50; H, 3.37; N, 23.40. Found: C, 53.69; H, 3.59; N, 23.12.

The nuclear magnetic resonance spectrum was consistent with the assigned structure.

EXAMPLE XI

To a solution of 43.2 g of 2-diethylaminoethylamine (N,N-diethylethylenediamine) in 400 ml of tetrahydrofuran was added 54 g of 2,4-dichloroquinazoline. The mixture was stirred at ambient temperature overnight. The reaction mixture was evaporated almost to dryness and the residue was suspended in water. The aqueous medium was made alkaline with dilute sodium hydroxide and was extracted several times with ether. The combined ether extracts were washed with water, dried over anhydrous sodium sulfate, and filtered. The filtrate was saturated with anhydrous hydrogen chloride. The solid which precipitated was isolated by filtration and then was recrystallized from ethanol and ether, giving 53.8 g of 2-chloro-4-(2-diethylaminoethylamino)-quinazoline dihydrochloride which decomposed at 152°. The following analytical data were obtained:

Calculated for $C_{14}H_{21}N_4Cl_3$: C, 47.81; H, 6.02; N, 15.93. Found: C, 47.63; H, 6.01; N, 15.64.

The nuclear magnetic resonance spectrum was consistent with the assigned structure.

EXAMPLE XII

A mixture of 10 g of 2,4-dichloroquinazoline, 4.5 g of pyrrolidine, 6.3 g of triethylamine, and 200 ml of tetrahydrofuran was heated at reflux overnight. The solvent was evaporated and the drak brown residue was dissolved in ether. The ether solution was washed with water, dried over anhydrous sodium sulfate, and filtered. The ether was evaporated and the residue was recrystallized from ethanol giving 4 g of 2-chloro-4-pyrrolidinylquinazoline; m.p 170°-172°: The following analytical data were obtained:

Calculated for $C_{12}H_{12}ClN_3$: C, 61.66; H, 5.17; N, 17.98. Found: C, 61.65; H, 5.46; N, 18.00.

The nuclear magnetic resonance spectrum was consistent with the assigned structure.

EXAMPLE XIII

The procedure of Example XII was repeated, except that the pyrrolidine was replaced with 5.3 g of piperidine. Also, the crude material obtained upon evaporation of the ether solution was recrystallized from hexane. The yield of 2-chloro-4-piperidinoquinazoline was 10.6 g; m.p. 69°-72°. The following analytical data were obtained:

Calculated for $C_{13}H_{14}ClN_3$: C, 63.02; H, 5.69; N, 16.96. Found: C, 63.21; H, 5.56; N, 17.22.

The nuclear magnetic resonance spectrum was consistent with the assigned structure.

EXAMPLE XIV

Twenty grams of 2,4-dichloroquinazoline was suspended in 200 ml of ethanol. To this suspension was added 17.4 g of morpholine. A mildly exothermic reaction ensued with the concomitant dissolution of the suspended dichloroquinazoline. When the reaction subsided, after about 10 minutes, the mixture was heated at reflux for 15 minutes, and then was allowed to cool. The reaction mixture then was diluted with 800 ml of water. The solid which precipitated was collected by filtration and was washed with water. After drying, the solid was recrystallized from 1:2 benzene-hexane, to give 18.5 g of 2-chloro-4-morpholinoquinazoline; m.p. 103°–105°. The following analytical data were obtained:

Calculated for $C_{12}H_{12}ClN_3O$: C, 57.72; H, 4.84; N, 16.83. Found: C, 57.95; H, 5.01; N, 16.68.

The nuclear magnetic resonance spectrum was consistent with the assigned structure.

By means of the general procedure illustrated by Examples XI–XIV inclusive, the following compounds also were prepared:

2-Chloro-4-(diethylamino)quinazoline, in a yield of 91 percent; m.p. 68°–70°. The following analytical data were obtained:

Calculated for $C_{12}H_{16}ClN_3$: C, 60.63; H, 6.67; N, 17.68. Found: C, 60.87; H, 6.65; N, 17.58.

The nuclear magnetic resonance spectrum was consistent with the assigned structure.

2-Chloro-4-(1-adamantylamino)quinazoline, in a yield of 83 percent; m.p. 213°–215°. The following analytical data were obtained:

Calculated for $C_{18}H_{20}ClN_3$: C, 68.89; H, 6.42; N, 13.39. Found: C, 68.65; H, 6.64; N, 13.17.

The nuclear magnetic resonance spectrum was consistent with the assigned structure.

2-Chloro-4-(4-methylpiperazinyl)quinazoline monohydrochloride, in a yield of 60 percent; m.p. 314°–316° with decomposition. The following analytical data were obtained:

Calculated for $C_{13}H_{16}Cl_2N_4$: C, 52.19; H, 5.39; N, 18.73. Found: C, 51.95; H, 5.61; N, 18.52.

The nuclear magnetic resonance spectrum was consistent with the assigned structure.

EXAMPLE XV

A solution of 7 g of morpholine in 25 ml of tetrahydrofuran was added dropwise to a solution of 7.2 g of 2-chloro-4-aminoquinazoline in 75 ml of tetrahydrofuran. After the addition was completed, the mixture was heated at reflux overnight. The reaction mixture was evaporated to dryness and the residue was recrystallized twice from ethanol to give 5 g of 2-morpholino-4-aminoquinazoline; m.p. 216°–219°. The following analytical data were obtained.

Calculated for $C_{12}H_{14}N_4O$: C, 62.59; H, 6.13; N, 24.33. Found: C, 62.84; H, 6.26; N, 24.41.

The nuclear magnetic resonance spectrum was consistent with the assigned structure.

EXAMPLE XVI

A mixture of 5 g of 2-chloro-4-aminoquinazoline, 5 ml of 4-methylpiperazine, and 10 ml of ethanol was heated at reflux overnight. The reaction mixture was diluted with 200 ml of water, made alkaline with 15 ml of 50 percent sodium hydroxide solution, and extracted with 500 ml of ether. The ether extract was washed with water, dried over anhydrous sodium sulfate, and filtered. The ether was removed by evaporation. The residue was dissolved in 500 ml of dry ether and treated with excess hydrogen chloride. Filtration afforded 1.5 g of 2-(4-methylpiperazinyl)-4-aminoquinazoline hydrochloride; m.p. 333°–334° with decomposition. The following analytical data were obtained:

Calculated for $C_{13}H_{19}Cl_2N_5$: C, 49.38; H, 6.06; N, 22.15. Found: C, 48.99; H, 5.71; N, 22.12.

The nuclear magnetic resonance spectrum was consistent with the assigned structure.

EXAMPLE XVII

A mixture of 5 g of 2-chloro-4-diethylaminoquinazoline, 5 ml of morpholine, and 10 ml of ethanol was heated at reflux for 16 hours. The product was isolated as described in Example XVI. The yield of 2-morpholino-4-diethylaminoquinazoline hydrochloride, m.p. 198°–200°, was 6 g. The following analytical data were obtained:

Calculated for $C_{16}H_{23}ClN_4O$: C, 59.53; H, 7.18; N 17.35. Found: C, 59.32; H, 7.23; N, 17.64.

The nuclear magnetic resonance spectrum was consistent with the assigned structure.

EXAMPLE XVIII

A solution of 6.4 g of pyrrolidine in 50 ml of tetrahydrofuran was added to 10 g of 2-chloro-4-(2-diethylaminoethylamino)quinazoline hydrochloride in 100 ml of tetrahydrofuran. The reaction mixture was stirred at ambient temperature for about one hour and then was heated for 5 hours. The reaction mixture was poured into ice-water, made alkaline by the addition of dilute aqueous sodium hydroxide solution, and extracted with ether. The ether extract was washed with water, dried over anhydrous sodium sulfate, filtered, and evaporated. The residue, a gummy solid, was triturated with about 5 ml of hexane, and the resulting mixture was chilled overnight in a refrigerator. The mixture then was filtered and the solid obtained was recrystallized from aqueous ethanol to give 2 g of 2-pyrrolidinyl-4-(2-diethylaminoethylamino)quinazoline; m.p. 87°–90°. The following analytical data were obtained:

Calculated for $2_{18}H_{27}N_5$: C, 68.97; H, 8.68; N, 22.45. Found: C, 68.72; H, 8.39; N, 22.10.

The nuclear magnetic resonance spectrum was in agreement with the assigned structure.

EXAMPLE XIX

A solution of 5 g of morpholine in 50 ml of tetrahydrofuran was added to 6.8 g of 2-chloro-4-(2-diethylaminoethylamino)quinazoline in 50 ml of tetrahydrofuran. The reaction mixture was heated at reflux overnight and then evaporated to dryness. The residue was suspended in dilute sodium hydroxide solution and the crude product was extracted into ether. The ether extract was washed with water, dried over anhydrous sodium sulfate, filtered, and the filtrate evaporated to dryness. Attempts to crystallize the residue were unsuccessful. The residue then was distilled under reduced pressure. The distillate was dissolved in ether and treated with hydrogen chloride. The product was collected by filtration and dried, giving 3.7 g of 2-morpholino-4-(2-diethylaminoethylamino)quinazoline hydrochloride; m.p. 216°-220°. The following elemental analysis was obtained:

Calculated for $C_{18}H_{29}Cl_2N_5O\cdot H_2O$: C, 51.42; H, 7.44; N, 16.66. Found: C, 51.44; H, 7.38; N, 16.30.

The nuclear magnetic resonance spectrum was consistent with the assigned structure.

EXAMPLE XX

A mixture of 5 g of 2-chloro-4-(1-adamantylamino)-quinazoline, 5 ml of morpholine, and 10 ml of ethanol was refluxed for 16 hours. The reaction mixture was suspended in 100 ml of 6 N hydrochloric acid. The precipitate which resulted was collected by filtration and recrystallized twice from 95 percent ethanol, giving 3.5 g of 2-morpholino-4-(1-admantylamino)quinazoline hydrochloride; m.p. 319°-321°. The following analytical data were obtained:

Calculated for $C_{22}H_{29}ClN_4O$: C, 65.90; H, 7.29; N, 13.97. Found: C, 65.88; H, 7.30; N, 14.08.

The nuclear magnetic resonance spectrum was consistent with the assigned structure.

EXAMPLE XXI

A mixture of 4 g of 2-chloro-4-morpholinoquinazline, 5 ml of ethylenediamine, and 10 ml. of ethanol was heated at reflux overnight. The reaction mixture was diluted with 200 ml of water made alkaline with 15 ml of 50 percent aqueous sodium hydroxide solution, and extracted with one liter of ether. The ether extract was washed with water, dried over anhydrous sodium sulfate, filtered, and evaporated. The residue was dissolved in 500 ml of ether and treated with excess hydrogen chloride. The crude product was collected by filtration and recrystallized from ether-ethanol, to give 1 g of 2-(2-aminoethylamino)-4-morpholinoquinazoline dihydrochloride; m.p. 292°-294° with decomposition. The following analytical data were obtained: Calculated for $C_{14}H_{21}Cl_2N_5O$: C, 48.56; H, 6.11; N, 20.23. Found: C, 48.28; H, 5.86; N, 20.21.

EXAMPLE XXII

A mixture of 5 g of 2-chloro-4-(4-methylpiperazinyl)-quinazoline, 5 ml of morpholine, and 10 ml of ethanol was refluxed for 16 hours. The reaction mixture was diluted with 200 ml of water, make alkaline with 10 ml of 50 percent aqueous sodium hydroxide solution, and extracted with ether. The ether extract was washed with water, dried over anhydrous sodium sulfate, filtered, and evaporated to dryness. The residue was dissolved in 500 ml of ether. The ethereal solution was treated with excess hydrogen chloride and the resulting precipitate was collected by filtration. The crude product was recrystallized twice from 95 percent ethanol, giving 3 g of 2-morpholino-4-(4-methylpiperazinyl)-quinazoline dihydrochloride, dihydrate; m.p. 310°-312° with decomposition. The following analytical data were obtained:

Calculated for $C_{17}H_{25}Cl_2N_5O\cdot 2H_2O$: C, 48.40; H, 6.88; N, 16.60. Found: C, 48.65; H, 6.97; N, 16.80

The nuclear magnetic resonance spectrum was consistent with the assigned structure.

What is claimed is:

1. A method of inhibiting platelet aggregation in a warm-blooded animal in need of such inhibition which comprises parenterally administering to said animal an effective and nontoxic amount of a compound of the formula,

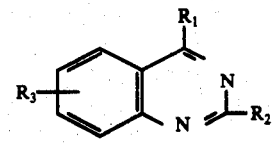

wherein $R_1$ and $R_2$ are monovalent groups independently selected from the group consisting of a.

wherein $R_4$ and $R_5$ independently are selcted from the group consisting of hydrogen, $C_1$-$C_6$ alkyl, and cycloalkyl having fewer than about 12 carbon atoms, with the proviso that both $R_4$ and $R_5$ cannot be cycloalkyl;

b.

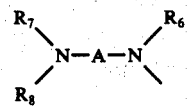

wherein $R_6$, $R_7$, and $R_8$ independently are selected from the group consisting of hydrogen and $C_1$-$C_6$ alkyl, and A is a divalent organic group having from about two to about six carbon atoms such that the two nitrogen atoms are separated by at least two carbon atoms; and c. monocyclic heterocyclic-amino consisting of substituted or unsubstituted five- or six-membered single heterocyclic rings having no more than about 12 atoms and containing one nitrogen hetero atom and one oxygen hetero atom as the only hetero atoms; with the proviso that at least one of $R_1$ and $R_2$ must be selected from group (c); and $R_3$ is selected from the group consisting of hydrogen, halogen, and $C_1$-$C_3$ alkyl; and physiologically-acceptable salts thereof.

2. The method of claim 1, wherein $R_4$ and $R_5$ independently are selected from the group consisting of hydrogen, $C_1$-$C_3$ alkyl, and cycloalkyl, with the proviso that when either $R_4$ or $R_5$ is hydrogen, the remaining group cannot be $C_1$-$C_3$ alkyl.

3. The method of claim 2, wherein $R_4$ and $R_5$ both are either hydrogen or identical $C_1$-$C_3$ alkyl groups, or one of $R_4$ and $R_5$ is hydrogen and the remaining group is cycloalkyl.

4. The method of claim 1, wherein $R_6$, $R_7$, and $R_8$ independently are selected from the group consisting of hydrogen and $C_1$-$C_3$ alkyl and A is a polymethylene group.

5. The method of claim 4, wherein $R_6$ is hydrogen and $R_7$ and $R_8$ both are identical $C_1$-$C_3$ alkyl groups.

6. The method of claim 1, wherein $R_3$ is selected from the group consisting of hydrogen, chlorine, and methyl.

7. The method of claim 6, wherein $R_3$ is in the 6-position.

8. A method of inhibiting platelet aggregation in a warm-blooded animal in need of such inhibition which comprises parenterally administering to said animal an effective and non-tonic amount of a compound of the formula,

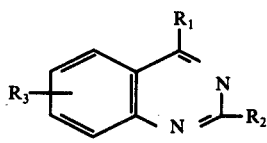

wherein $R_1$ and $R_2$ are monovalent groups independently selected from the group consisting of a.

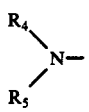

wherein $R_4$ and $R_5$ independently are selected from the group consisting of hydrogen, $C_1$-$C_3$ alkyl, and cycloalkyl having fewer than about 12 carbon atoms, with the proviso that when either $R_4$ or $R_5$ is hydrogen the remaining group cannot be $C_1$-$C_3$ alkyl, and that both $R_4$ and $R_5$ cannot be cycloalkyl;

b.

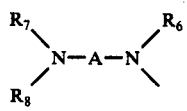

wherein $R_6$, $R_7$, and $R_8$ independently are selected from the group consisting of hydrogen and $C_1$-$C_3$ alkyl and A is a polymethylene group; and c. monocyclic heterocyclic-amino consisting of substituted or unsubstituted five- or six-membered single hterocyclic rings having no more than about 12 atoms and containing one nitrogen hetero atom and one oxygen hetero atom as the only hetero atoms; with the proviso that at least one of $R_1$ and $R_2$ must be selected from group (c); and $R_3$ is selected from the group consisting of hydrogen, chlorine, and methyl, and physiologically-acceptable salts thereof.

9. The method of claim 8, wherein $R_4$ and $R_5$ both are either hydrogen or identical $C_1$-$C_3$ alkyl groups, or one of $R_4$ and $R_5$ is hydrogen and the remaining group is cycloalkyl.

10. The method of claim 8, wherein $R_6$ is hydrogen and $R_7$ and $R_8$ both are identical $C_1$-$C_3$ alkyl groups.

11. The method of claim 8, wherein $R_3$ is in the 6-position.

12. A method of inhibiting platelet aggregation in a warm-blooded animal in need of such inhibition which comprises parenterally administering to said animal an effective and nontoxic amount of a compound of the formula,

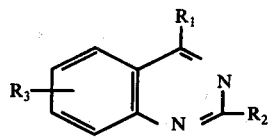

wherein $R_1$ and $R_2$ are monovalent groups independently selected from the group consisting of a.

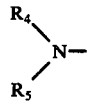

wherein $R_4$ and $R_5$ both are either hydrogen or identical $C_1$-$C_3$ alkyl groups, or one of $R_4$ and $R_5$ is hydrogen and the remaining group is cycloalkyl having fewer than about 12 carbon atoms;

b.

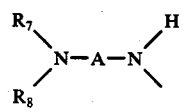

wherein $R_7$ and $R_8$ both are identical $C_1$-$C_3$ alkyl groups and A is a polymethylene group; and c. monocyclic heterocyclic-amino consisting of unsubstituted five- or six-membered single heterocyclic rings containing one nitrogen hetero atom and one oxygen hetero atom as the only hetero atoms; with the proviso that at least one of $R_1$ and $R_2$ must be selected from group (c); and $R_3$ is selected from the group consisting of hydrogen, chlorine, and methyl and is in the 6-position; and physiologically-acceptable salts thereof.

13. The method of claim 12, wherein the compound is 2-morpholino-4-(diethylamino)quinazoline.

14. The method of claim 12, wherein the compound is 2-morpholino-4-(2-diethylaminoethylamino)quinazoline.

15. The method of claim 12, wherein the compound is 2-(2-aminoethylamino)-4-morpholinoquinazoline.

16. The method of claim 12, wherein the compound is 2,4-bismorpholinoquinazoline.

17. The method of claim 12, wherein the compound is 2-morpholino-4-(4-methylpiperazinyl)quinazoline.

18. The method of claim 12, wherein the compound is 2-(4-methylpiperazinyl)-4-morpholinoquinazoline.

19. The method of claim 12, wherein the compound is 2-morpholino-4-aminoquinazoline.

20. The method of claim 12, werein the compound is 2,4-bismorpholino-6-methylquinoline.

21. The method of claim 12, wherein the compound is 2,4-bismorpholino-6-chloroquinazoline.

22. The method of inhibiting platelet aggregation in a warm-blooded animal in need of such inhibition which comprises enterally administering to said animal an effective and nontoxic amount of 2-morpholino-4-(2-diethylaminoethylamino) quinazoline and physiologically-acceptable salts thereof.

23. The method of claim 22, wherein administration is oral.

* * * * *

UNITED STATES PATENT OFFICE
CERTIFICATE OF CORRECTION

Patent No. 4,048,312    Dated September 13, 1977

Inventor(s) William B. Lacefield

It is certified that error appears in the above-identified patent and that said Letters Patent are hereby corrected as shown below:

Column 4, line 32: "r$_3$" should read --R$_3$--.

Column 4, line 52: "2,4bis" should read --2,4-bis--.

Column 4, line 57: "4-propyl" should read --5-propyl--.

Column 4, line 66: "quinoline" should read --quinazoline--.

Column 5, line 6: "2-aminoethylamino-6" should read --2-aminoethylamino-4-morpholino-6--.

Column 5, line 20: "4-morpholine" should read --4-morpholino--

Column 9, line 64: "cellulose" should read --celluose--.

Column 14, line 49: "drak" should read --dark--.

Column 15, line 38: "H, 6.64" should read --H, 6.65--.

Column 16, line 24: "$C_{16}H_{23}ClN_4o$" --$C_{16}H_{23}ClN_4O$--.

Column 16, line 36: "heated for 5" should read --heated at reflux for 5--.

Column 16, line 48: "Calculated for $2_{18}H_{27}$" should read --Calculated for $C_{18}H_{27}$--.

Column 16, line 48: "N, 22.45" should read --N, 22.34--.